United States Patent [19]

Meek et al.

[11] Plant 4,586

[45] Jul. 29, 1980

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 20,772

[22] Filed: Mar. 15, 1979

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—Donald D. Jeffery

[57] ABSTRACT

A chrysanthemum plant known by the cultivar name Applause having flat capitulum form; pompon capitulum type; yellow green (immature) to dark yellow (mature) ray floret color; diameter across face of capitulum ranging from 30 to 50 mm at maturity; uniform eight week photoperiodic flowering response to short days; short plant height when grown as a pinched spray pot, and semi-spreading branching pattern.

3 Drawing Figures

The present invention comprises a new and distinct cultivar of *Chrysanthemum morifolium,* Ramat., hereinafter referred to by the cultivar name Applause.

Applause is a product of a planned breeding program which had the objective of creating a new chrysanthemum cultivar with pompom capitulum type, yellow ray floret color, eight or nine week flowering response, and the ability to produce commercially acceptable quality in year round pot mum programs. Such traits in combination were not present in previously available commercial cultivars.

Applause was originated in a controlled hybridization program in 1976 in Barberton, Ohio. The female parent was #75235006, an unnamed pink decorative seedling originated from hybridazation of #73100001 (unnamed seedling) and #70101018 (unnamed seedling). The male parent of Applause was #75222005, an unnamed yellow pompon seedling originated from a hybridization of Pearls, disclosed in U.S. Plant Pat. No. 3,970 and #70293005 (unnamed seedling).

Applause was discovered and selected as one flowering plant within the progeny of the stated cross by Jack M. Meek and William E. Duffett on Sept. 7, 1977 in a controlled environment in Salinas, Calif.

The first act of asexual reproduction of Applause was accomplished when vegetative cuttings were taken from the initial selection in January, 1978 in a controlled environment in Salinas, Calif., by a technician working under formulations established and supervised by Jack M. Meek and William E. Duffett. Continued asexual reproduction by vegetative cuttings for evaluative tests in flowering and stock programs in conjunction with horticultural examination of selected plants initiated April 28, 1978, has demonstrated that the combination of characteristics as herein disclosed for Applause are firmly fixed and are retained through successive generations of asexual reproduction.

Applause has not been observed under all possible environmental conditions. The phenotype may vary significantly with variations in environment such as temperature, light intensity, and daylength. The following observations, measurements and comparisons describe plants grown in Salinas, Calif. under greenhouse conditions which approximate those generally used in commercial practice.

The following traits have been repeatedly observed and are determined to be basic characteristics of Applause which in combination distinguish this chrysanthemum as a new and distinct cultivar:

(1) flat capitulum form.

(2) pompon capitulum type.

(3) yellow-green (immature) to dark yellow (mature) ray floret color.

(4) diameter across face of capitulum ranging from 30 to 50 mm at maturity.

(5) uniform eight week photoperiodic flowering response to short days.

(6) short plant height (requiring 2–3 long day weeks prior to pinch and short days, and 1 application 2500 ppm B-9 SP 14 to 21 days after the beginning of short days to attain a flowered plant height of 30 to 35 cm).

(7) semi-spreading branching pattern.

The accompanying photographic drawings show typical inflorescence and foliage characteristics of Applause. Sheet 1 is a color photograph of Applause grown as a pinched spray pot. Some difficulty was encountered in obtaining accurate color representation, the actual flower color being less red and more yellow than the photographic depiction. The color readings within the following description are, however, correct. Sheet 2 is a black and white photograph showing three views of the inflorescence of Applause. Sheet 3 is a black and white photograph showing the foliage of Applause at three stages of growth.

Of the many commercial cultivars known to the present inventors, the most similar existing cultivars in comparison to Applause are Sunny Mandalay, U.S. Plant Pat. No. 3,231 and Yellow Torch, U.S. Plant Pat. No. 3,421. Reference is made to attached Chart A which compares certain characteristics of Applause to those same characteristics of Sunny Mandalay and Yellow Torch.

General comparisons are as follows:

1. In comparison to Sunny Mandalay, Applause has different capitulum form, different capitulum type, smaller diameter across face of capitulum, shorter plant height, and shorter flowering response period. The ray floret color and branching pattern of Applause are similar to those same characteristics of Sunny Mandalay.

2. In comparison to Yellow Torch, Applause has less bronzy ray floret color with cool (below 60° F.) flowering temperatures, different capitulum type, more spreading branching pattern, smaller diameter across face of capitulum, and shorter flowering response period. The capitulum form and plant height of Applause are similar to those same characteristics of Yellow Torch.

In the following description color references are made to A Limit Color Cascade by the Munsell Company, 1972 edition. The color values were determined between 2:00 p.m. and 2:30 p.m. on Jan. 30, 1979 under 50 foot-candle light intensity at Salinas, Calif.

Classification:

*Botanical.*—*Chrysanthemum morifolium,* Ramat., cv Applause.

*Commercial.*—Pinched spray pot mum.

I. INFLORESCENCE

A. Capitulum:

*Form.*—Flat.

*Type.*—Pompon.

*Diameter across face.*—30 to 50 mm.

B. Corolla of ray florets:

*Color (abaxial).*—24-3 (immature) to 25-6 to 25-5 (mature).

*Color (adaxial).*—25-4 to 25-3.

C. Reproductive organs:

*Gynoecium.*—Present in both ray and disc florets.

*Androecium.*—Present only in disc florets; scant pollen.

II. PLANT

A. General appearance:

*Height.*—Short (pot mum culture).

*Branching pattern.*—Semi-spreading.

B. Foliage:

*Color (abaxial).*—Approximately 21-14.

*Color (adaxial).*—21-13 overlaid with white.

Chart A

Comparison of Applause, Sunny Mandalay and Yellow Torch

| Cultivar | Ray Floret Color | Capitulum Form and Type | Branching Pattern | Diameter Across Face of Capitulum | Plant Height | Flowering Response Period |
|---|---|---|---|---|---|---|
| Applause | Dark Yellow | Flat Pompon | Semi-Spreading | 30 to 50 mm. | Short | 8 week |
| Sunny Mandalay | Dark Yellow | Semi-incurved Decorative | Semi-Spreading | 85 to 100 mm. | Medium | 10 week |
| Yellow Torch | Dark Yellow with bronzy overtones | Flat Decorative | Semi-upright | 75 to 90 mm. | Short | 9 week |

Comparisons made of plants grown as pinched spray pots in Salinas, California

We claim:

1. A new and distinct cultivar of *Chrysanthemum morifolium,* Ramat., plant as shown and described, known by the cultivar name Applause and particularly characterized as to uniqueness by the combined characteristics of flat capitulum form; pompon capitulum type; yellow green (immature) to dark yellow (mature) ray floret color; diameter across face of capitulum ranging from 35 to 50 mm at maturity; uniform eight week photoperiodic flowering response to short days; short plant height when grown as a pinched spray pot, and semi-spreading branching pattern.

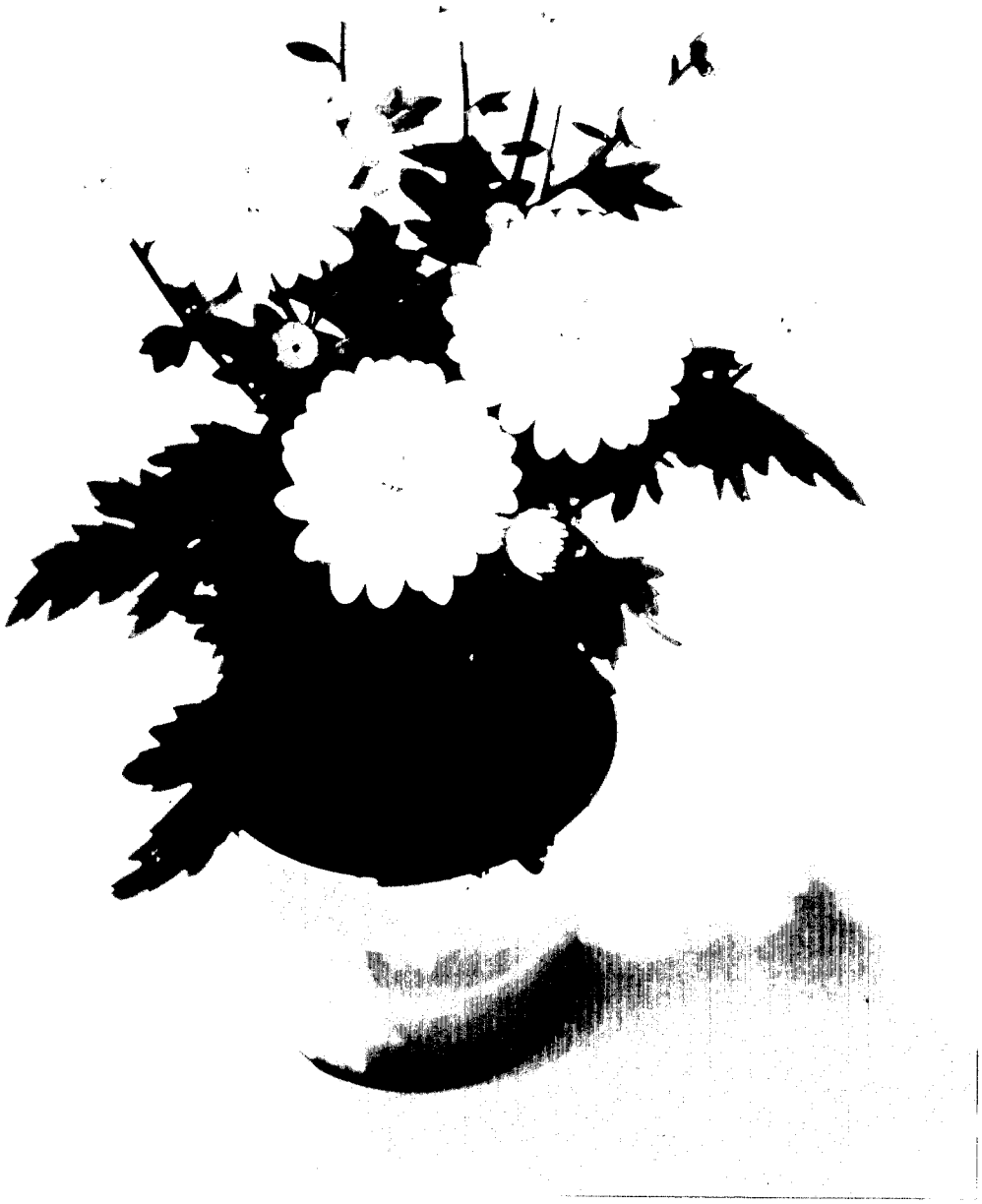

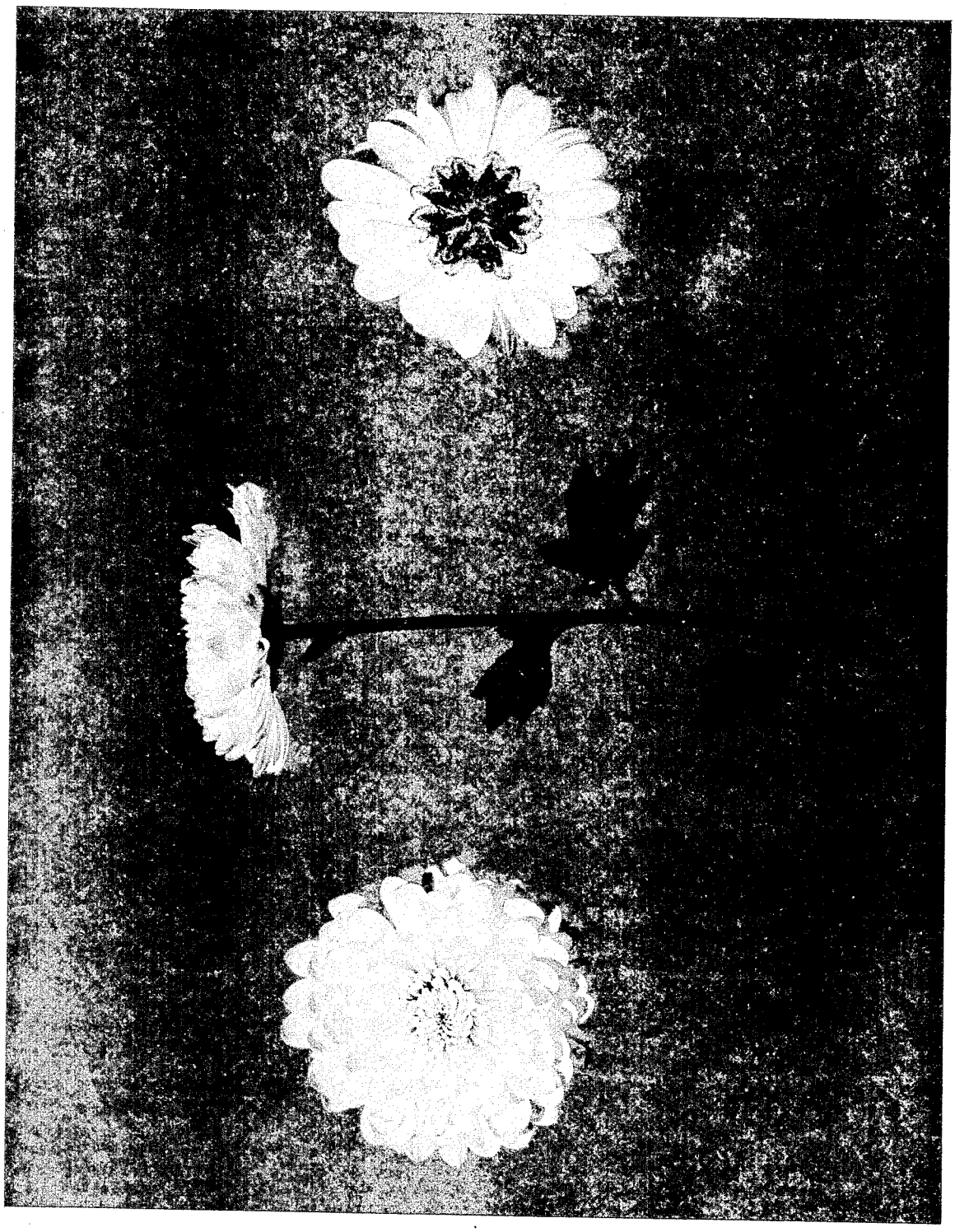

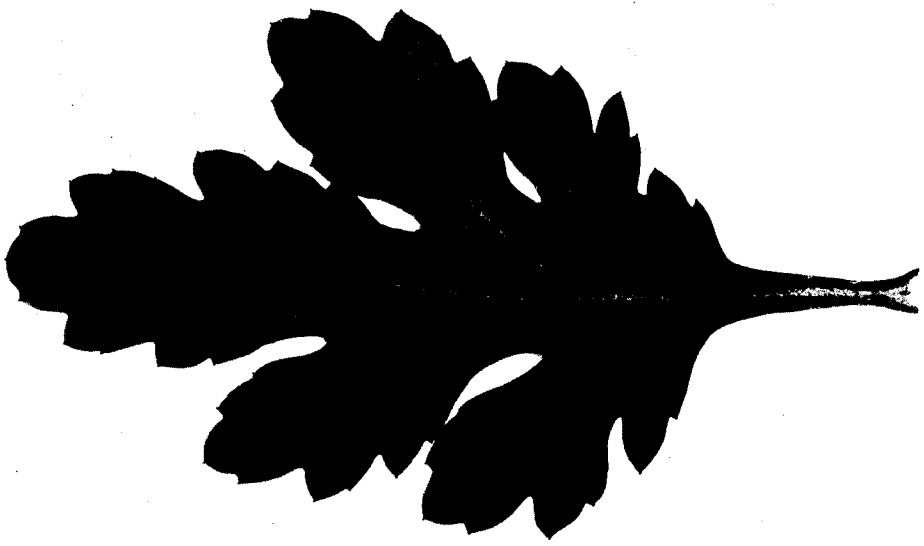
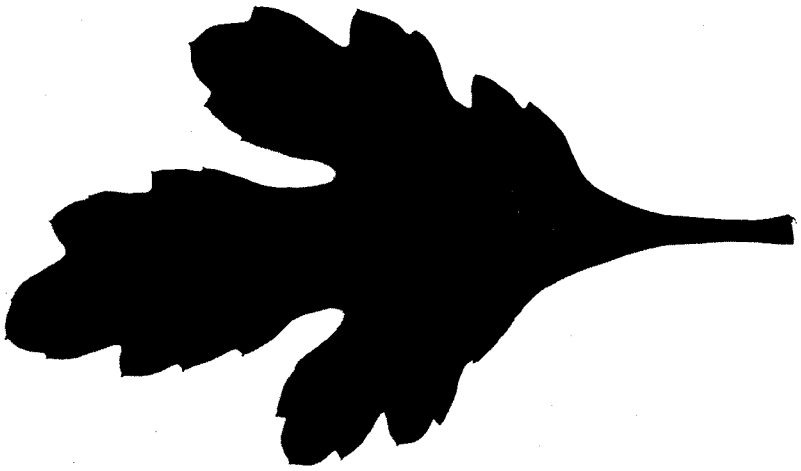
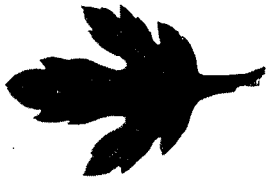

* * * * *